United States Patent [19]

Ueda

[11] 4,180,733
[45] Dec. 25, 1979

[54] INFRARED RAY GAS ANALYZING APPARATUS

[75] Inventor: Shinya Ueda, Kawasaki, Japan

[73] Assignee: Fuji Electric Co., Ltd., Kawasaki, Japan

[21] Appl. No.: 912,144

[22] Filed: Jun. 2, 1978

[30] Foreign Application Priority Data

Jun. 2, 1977 [JP] Japan ............................ 52-70714[U]

[51] Int. Cl.² .......................................... G01N 21/26
[52] U.S. Cl. .................................................. 250/345
[58] Field of Search ................. 250/343, 344, 345, 373

[56] References Cited

U.S. PATENT DOCUMENTS

| | | | |
|---|---|---|---|
| 3,193,676 | 7/1965 | Smart | 250/345 |
| 4,004,146 | 1/1977 | Blunck | 250/345 |

*Primary Examiner*—Davis L. Willis
*Attorney, Agent, or Firm*—Sughrue, Rothwell, Mion, Zinn and Macpeak

[57] ABSTRACT

An infrared type gas analyzer having measuring and reference cells is equipped with alternately switchable valves so that the cells can alternate acting as the measuring and reference cells. The output of the detector is stored for each configuration and these outputs are subtracted from one another to provide the output of the analyzer.

2 Claims, 12 Drawing Figures

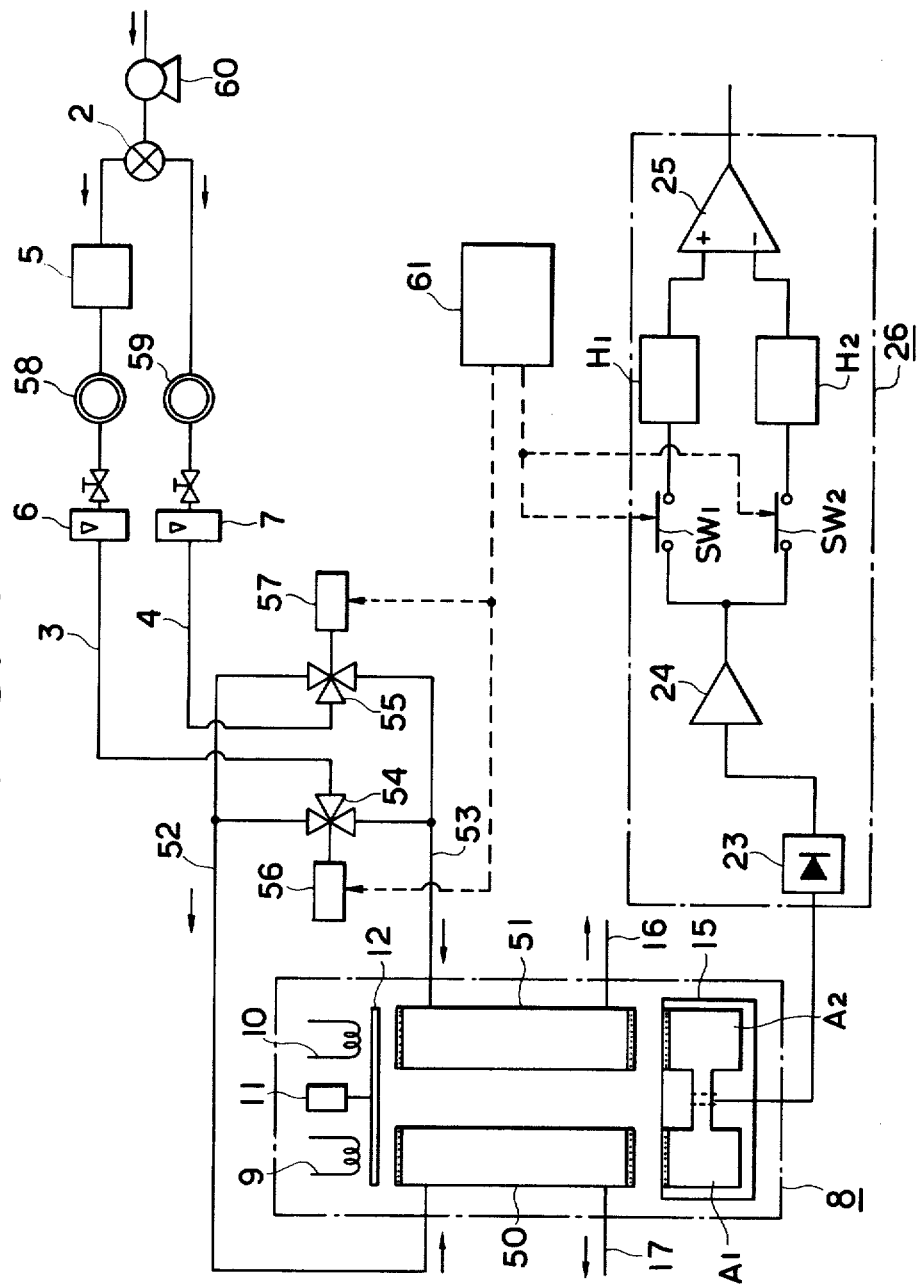

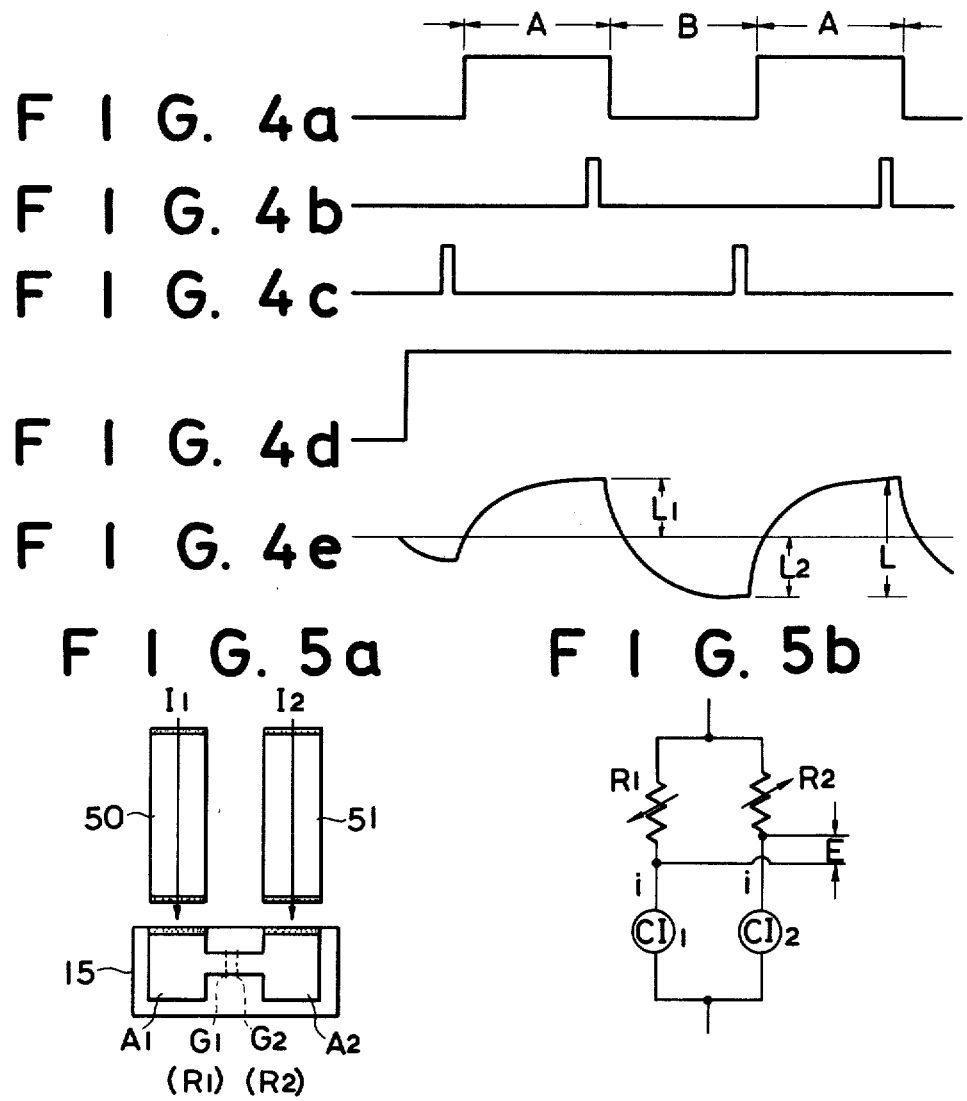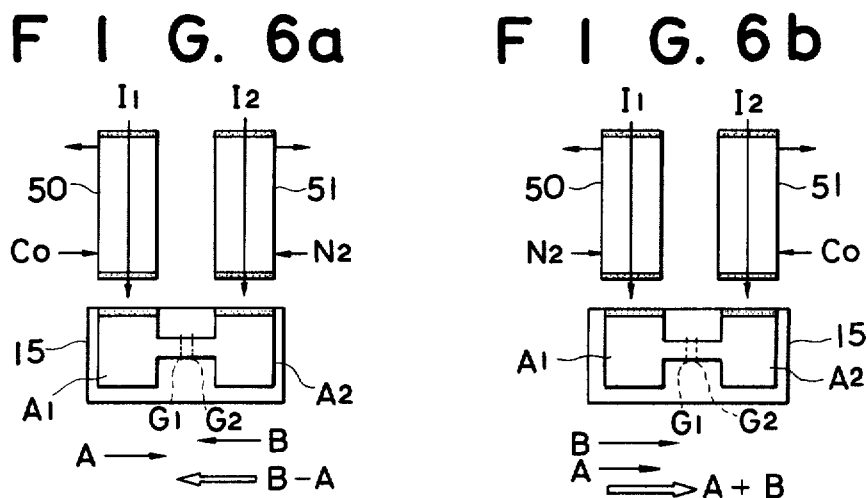

INFRARED RAY GAS ANALYZING APPARATUS

BACKGROUND OF THE INVENTION

This invention relates to an infrared ray gas analyzing apparatus in which the infrared ray wavelength absorption characteristics inherent in various gases are utilized for measuring the amount of energy absorbed, to thereby subject a sample gas to quantitative analysis.

In general, an infrared ray gas analyzer is extensively used for analyzing various gases because it is excellent in stability and reliability. For instance, it is used for detecting a minute quantity gas contained in the air, or the low density CO gas in the air for the purpose of circumstance security, pollution prevention and pollution monitoring.

FIG. 1 is a schematic diagram showing a conventional infrared ray analyzer for measuring CO gas. A sample gas, for instance the air, is distributed from a sampling conduit 1 through a branch pipe 2 to a reference gas conduit 3 and to a sample gas conduit 4. The reference conduit 3 is provided with a converter 5 and a flow meter 6, and is connected to a reference cell 13 in an infrared ray analyzer 8. Accordingly, the gas in the conduit 3 flows into the reference cell 13 and flows out of the latter through a conduit 16 connected to the reference cell 13. The converter 5 is a small combustion furnace where CO gas is burnt at a lower temperature with the aid of a catalyst so that the CO gas is converted into $CO_2$ gas. The flow meter 6 is provided with a flow rate control valve for supplying a certain quantity of reference gas to the analyzer 8. On the other hand, the sample gas conduit 4 is provided with a flow meter 7. After a certain quantity of sample gas is supplied to a sample cell 14 in the analyzer 8, it is discharged through an exhaust pipe 17 connected to the cell 14.

A measurement light beam emitted by an infrared ray source 9 is subjected to absorption in correspondence to the density of the analysis gas CO in the sample gas in the sample cell 14. On the other hand, a reference light beam emitted by an infrared ray source 10 is passed through the reference cell 13 without being absorbed, because there is no CO gas in the reference gas. The measurement light beam passed through the sample cell 14 and the reference light beam passed through the reference cell 13 are alternately or simultaneously interrupted by a chopper 12 which is rotated at a constant speed by a chopper motor 11, and a detector 15 detects the difference in light quantity between the reference light beam and the measurement light beam as an electrical pulsating current, which is rectified and amplified. The current thus treated is outputted by the detector 15. Thus, the difference in light quantity corresponds to the density of the analysis gas in the sample gas.

In an infrared ray gas analyzer of this type, the decrease in light quantity of the measurement light beam with respect to the light quantity of the reference light beam is provided as its output. Therefore, the detection sensitivity in analyzing a low density gas is insufficient and, furthermore, it is difficult to increase the detection sensitivity. Furthermore, the conventional infrared ray gas analyzer is disadvantageous in the following points. The mist (polluting material) in the sample gas is deposited on the inside surface of the sample cell 14, which lowers the reflection and transmittance conditions. The gas created when the sample gas is subjected to reaction through the converter 5 pollutes, in the form of mist, the reference cell 13, which also leads to variations of the reflection conditions. As a result, the optical balance is lost, which may cause zero point drift.

Shown in FIG. 2 is another infrared ray gas analyzer, in which those components having the same functions as those in FIG. 1 are designated by the same reference characters. A sample gas conduit 18 and a reference gas conduit 19 are switched at predetermined time intervals by a three-way valve 20 driven by a valve driving device 21, to thereby be connected alternately to a gas conduit 22. As a result, the sample gas or the reference gas 19 is introduced into the sample cell 14 in the analyzer 8 and is discharged through the discharge pipe 17. A gas, for instance $N_2$ gas, which does not absorb infrared rays is sealed in the reference cell 13. When the sample gas conduit 18 is connected to the gas conduit 22 by operating the three-way valve 20, the measurement light beam emitted by the infrared ray source 9 is subjected to infrared ray absorption in correspondence to the density of the analysis gas in the sample gas in the sample cell 14; however, the reference light beam emitted by the infrared ray source 10 is not subjected to infrared ray absorption in the reference cell 13. Accordingly, the difference in light quantity between the measurement light beam passed through the sample cell 14 and the reference light beam passed through the reference bath 13 is detected by the detector 15, the output of which corresponds to the density of the analysis gas. When the output of the detector becomes stable, a switch SW1 is closed. As a result, the output of the detector amplified by means of a rectifier 23 and an amplifier 24 is stored and held in an output holding circuit H1. Then, in a predetermined period of time shorter than several minutes, the reference gas conduit 19 is connected to the gas circuit 22 by operating the three-way valve 20, as a result of which the reference gas (such as $N_2$ gas) is allowed to flow in the sample cell 14. In this case, the measurement light beam is not absorbed. Accordingly, the light quantity of the measurement light beam passed through the sample cell 14 is equal to that of the reference light beam passed through the reference cell 13, and the difference in light quantity detected by the detector 14 is zero. However, similarly as in the firstly mentioned conventional infrared ray gas analyzer, the inside surface of the sample cell 14 is contaminated by the polluting material in the sample gas, as a result of which the optical balance between the sample cell and the reference cell is lost, which may lead to the occurrence of the zero point drift. In order to eliminate the effect of this zero point drift, when under this condition the output of the detector 15 becomes stable, a switch SW2 is closed. As a result, the output of the detector is stored and held by an output holding circuit H2. Thus, a differential amplifier 25 obtains the difference between the outputs of the output holding circuits H1 and H2, thereby to output a measurement value (measurement signal). Therefore, the zero point drift caused by the optical unbalance between the sample cell 14 and the reference cell 13 is automatically corrected. Nevertheless, the conventional infrared ray gas analyzer is also disadvantageous in that, as the pollution of the sample cell 14 is increased thereby to cause a great optical unbalance on one side, the amount of correction of the zero point drift is increased. Furthermore, the detection sensitivity is still insufficient, similarly as in the analyzer shown in FIG. 1.

SUMMARY OF THE INVENTION

Accordingly, in view of the foregoing, an object of this invention is to provide an infrared ray gas analyzing apparatus in which the above-described difficulties accompanying a conventional one are eliminated, the detection sensitivity is increased to perform a low density gas analysis, and the zero point drift is eliminated.

The foregoing object and other objects of this invention have been achieved by the provision of an infrared ray gas analyzing apparatus which comprises: a first cell 50 irradiated by a first light beam of infrared rays; a second cell 51 irradiated by a second light beam of infrared rays; a detector 15 irradiated by said first and second light beams passed through said first and second cells; and a signal process circuit 26 having a first signal holding circuit H1, a second signal holding circuit H2 and a differential amplifier to which the outputs of said first and second signal holding circuits are applied, and in which a sample gas containing an analysis gas, and a reference gas are allowed to alternately and periodically flow in said first cell and said second cell at the same time, the output signal of said detector provided when the sample gas is allowed to flow in said first cell is held by said first signal holding circuit, the output signal of said detector provided when the sample gas is allowed to flow in said second cell is held by said second signal holding circuit, and the output signal of said differential amplifier is employed as a measure for the analysis gas in said sample gas.

BRIEF DESCRIPTION OF THE DRAWINGS

FIG. 3 is a schematic diagram showing an infrared ray gas analyzing apparatus according to this invention.

FIG. 4 is an explanatory diagram for a description of the operation of the apparatus according to the invention. More specifically, FIG. 4(a) shows the switching schedule of the three-way valves; FIG. 4(b), the switching operation schedule in a state A; FIG. 4(c), the switching operation schedule in a state B; FIG. 4(d), the sample gas density variation; and FIG. 4(e), the output of an amplifier in the apparatus.

FIG. 5 is an explanatory diagram for a description of a zero point drift, FIG. 5(a) showing a schematic diagram of the detector construction and FIG. 5(b) showing a circuit diagram of a detection circuit.

FIG. 6 is an explanatory diagram for a description of the detection sensitivity of the apparatus according to the invention, FIG. 6(a) showing a diagram for a description of the detection sensitivity in the state A, and FIG. 6(b) showing a diagram for a description of the detection sensitivity in the state B.

DETAILED DESCRIPTION OF THE INVENTION

One embodiment of this invention will be described in detail with reference to FIGS. 3 to 6.

Figure 1:
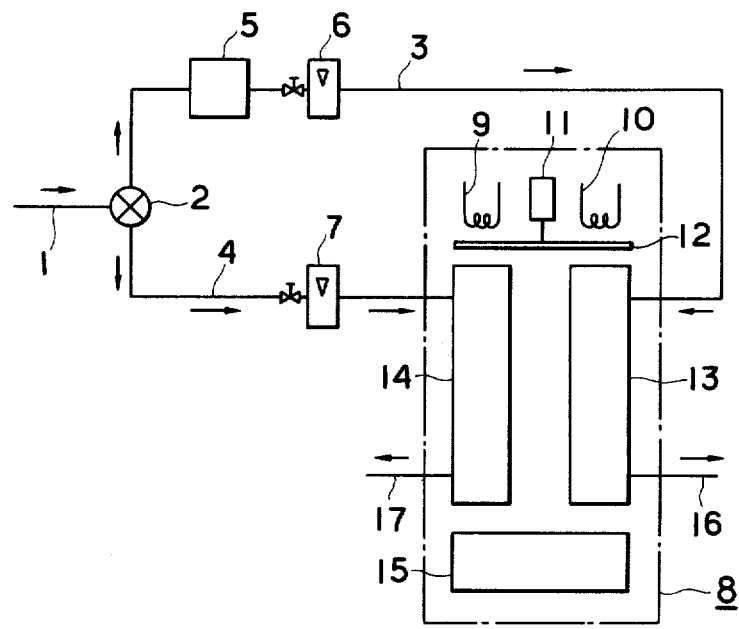
FIG. 1 is a schematic diagram showing a conventional infrared ray gas analyzing apparatus.
Figure 2:
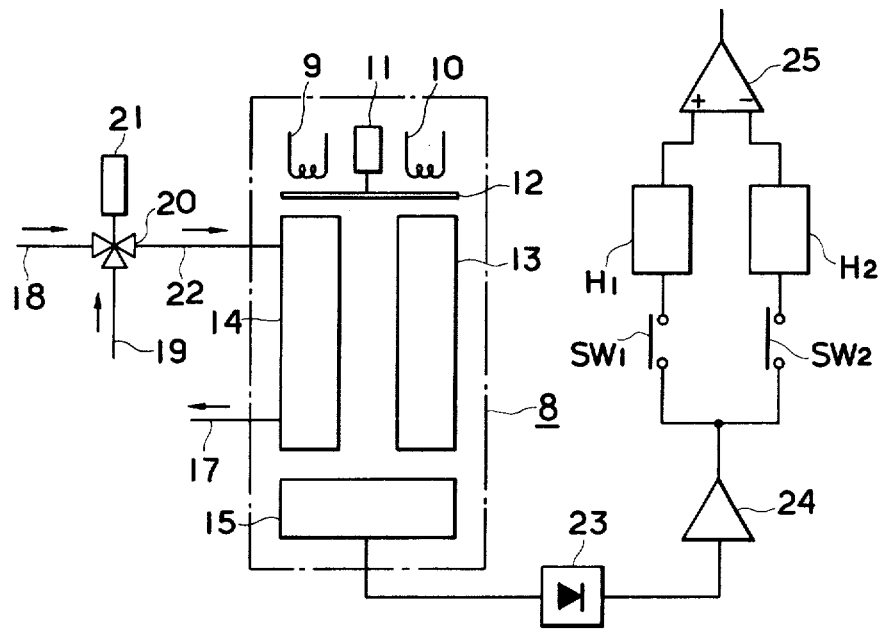
FIG. 2 is also a schematic diagram showing another conventional infrared ray gas analyzing apparatus.

FIG. 3 is an explanatory diagram outlining the embodiment of the invention, in which those components which have been described with reference to FIGS. 1 and 2 are therefore similarly numbered. A sample gas is sucked by a pump 60 and is distributed through a branch pipe 2 to a reference gas conduit 3 and a sample gas conduit 4. A converter 5, a filter 58 and a flow meter 6 are provided in the reference gas conduit 3. A three-way valve 54 is connected to the end of the reference gas conduit 3.

The three-way valve 54 is switched to a first conduit 52 or to a second conduit 53 by a valve driving device 56. The reference gas allowed to flow into the first conduit 52 by the switching operation of the three-way valve flows into a first cell 50 and flows out through an exhaust pipe 17. The reference gas allowed to flow into the second conduit 53 by the switching operation of the three-way valve flows into a second cell 51 and flows out of the cell through an exhaust pipe 16. On the other hand, a filter 59 and a flow meter 7 are provided in the sample gas conduit 4. A three-way valve 55 is connected to the end of the sample gas conduit 4. The three-way valve 55 is switched to the first conduit 52 or to the second conduit 53 by a valve driving device 57. The sample gas allowed to flow into the first conduit 52 by the switching operation of the three-way valve flows into the first cell 50 and flows out of the first cell through the exhaust pipe 17. The sample gas allowed to flow into the second conduit 53 by the switching operation of the three-way valve flows into the second cell 51 and flows out of the second cell through the exhaust pipe 16. When the three-way valve 55 is switched to the first conduit 52, and the three-way valve 54 is switched to the second concuit 53, the first light beam emitted from a first infrared ray source 9 is employed as a measurement light beam, and is subjected to infrared ray absorption according to the analysis gas density in the sample gas in the first cell 50. On the other hand, the second light beam emitted from a second infrared ray source 10 is employed as a reference light beam, and is not subjected to infrared ray absorption in the second cell 51. Accordingly, the difference in light quantity between the first light beam passed through the first cell 50 and the second light beam passed through the second cell 51 is detected by a detector 15, the output of which corresponds to the analysis gas density. This switching state will be referred to as "a state A," hereinafter.

When the three-way valve 55 is switched to the second conduit 53, while the three-way valve 54 is switched to the first conduit 52, the second light beam from the second infrared ray source 10 is employed as a measurement light beam and is subjected to infrared ray absorption according to the analysis gas density in the second cell 51, while the first light beam from the first infrared ray source 9 is employed as a reference light beam and is therefore not subjected to infrared ray absorption in the first cell 50. Accordingly, the difference in light quantity between the second light beam passed through the second cell 51 and the first light beam passed through the first cell 50 is detected by the detector 15, the output of which corresponds to the analysis gas density. This switching state will be referred to as "a state B," hereinafter.

In the state A described above, when the output of the detector 15 becomes stable, a switch SW1 in a signal process circuit 26 is closed. As a result, an output holding circuit H1 stores and holds the output of the detector which has been amplified by means of a rectifier 23 and an amplifier 24. Similarly, in the state B, when the output of the detector 15 becomes stable after substantially the same duration time as that in the state A, a switch SW2 in the signal process circuit 26 is closed, as a result of which the output of the detector, which has been amplified by means of the rectifier 23 and the amplifier 24, is stored and held in an output holding circuit H2. A differential amplifier 25 detects the difference between the output of the output holding circuit H1 and the output of the output holding circuit H2. The output of the differential amplifier 25 is employed as a measurement value (a measurement signal) of the analyzer. A sequencer 61 operates to supply switching signals to the valve driving devices 56 and 57 of the three-way valves 54 and 55 with the necessary timing, and to supply closure signals to the switches SW1 and SW2 with the necessary timing.

FIG. 4 shows diagrams for a description of the operation of the infrared ray type gas analyzing apparatus according to this invention. More specifically, FIG. 4(a) shows the switching schedule of the three-way valves; FIG. 4(b), the operation schedule of the switch SW1 in the state A; FIG. 4(c), the operation schedule of the switch SW2 in the state B; FIG. 4(d), the variation of the sample gas density; and FIG. 4(e), the output of the detector 15 in the analyzer 8. In FIG. 4, the sample gas density increases steppingly to a constant value.

The state A and the state B are switched alternately, and in this case the switch SW1 in FIG. 4(b) or the switch SW2 in FIG. 4(c) is closed when the output is stabilized. As a result, in the state A, the output value $L_1$ of the detector 15 is introduced to the holding circuit H1, while in the state B, the output value $L_2$ of the detector 15 is applied to the holding circuit H2. The outputs of the output holding circuits H1 and H2 are applied to the differential amplifier 25, as was described before. If it is assumed that the sample gas density is constant, the outputs $L_1$ and $L_2$ of the detector 15 are equal to each other. Accordingly, the output L of the differential amplifier 25 is the sum of the detector's output $L_1$ in the state A and the detector's output $L_2$ in the state B; that is, the output L is twice the output $L_1$ or $L_2$.

FIG. 5 is an explanatory diagram for a description of a zero point drift. More specifically, FIG. 5(a) is a schematic diagram showing the construction of the detector, while FIG. 5(b) is a circuit diagram of the detector. Referring to FIG. 5, when there is no analysis gas in the first and second cells 50 and 51, the first light beam passed through the first cell 50 is equal to the second light beam passed through the second cell 51, and therefore the output of the detector 15 is zero. When the first light beam $I_1$ is not equal in light quantity to the second light beam $I_2$ at the start, an output corresponding to the zero point drift occurs in the output of the detector 15. The detector 15 has detection cells $A_1$ and $A_2$ in which the same gas as the analysis gas in the detector 15 is sealed. when these light beams $I_1$ and $I_2$ are applied to the cells $A_1$ and $A_2$, the temperatures of the cells are increased and become different according to the difference in light quantity absorption, as a result of which the pressure, for example, in the detection cells $A_1$ becomes higher than that of the detection cells $A_2$. Thermal detection elements $G_1$ and $G_2$ are provided substantially at the center of a passage connecting the detection cells $A_1$ to the detection cells $A_2$. The thermal detection elements $G_1$ and $G_2$ are opposed with a small distance therebetween, and are heated by a constant current applied thereto. If it is assumed that the light quantity of the first light beam $i_1$ is greater than that of the second light beam $I_2$, in spite of the fact that there is no analysis gas in the first and second cells 50 and 51, the sealed gas is caused to flow from the detection bath $A_1$ to the detection bath $A_2$, as a result of which resistance variation takes place in the detection elements $G_1$ and $G_2$.

First, the element $G_1$ is subjected to thermal absorption by the sealed gas, as a result of which the element $G_1$ is cooled, and its electrical resistance is decreased. On the other hand, the element $G_2$ is heated by the flow of the sealed gas the temperature of which has been increased by absorbing the heat of the element $G_1$, as a result of which the electrical resistance of the element $G_2$ is increased.

When constant currents i are supplied to the elements by constant current devices $CI_1$ and $CI_2$, an output E provided in the detection circuit is:

$$E = R_1 i - R_2 i \qquad (1)$$

where $R_1$ is the resistance of the element $G_1$ obtained when its initial resistance R is subjected to temperature fall, and $R_2$ is the resistance of the element $G_2$ obtained when its initial resistance R is subjected to temperature rise.

In this case, $$R_1 = R - \Delta R, \text{ and } R_2 = R + \Delta R \qquad (2)$$

where $\Delta R$ is the resistance variation due to the temperature rise or fall of the elements $G_1$ and $G_2$.

Therefore, Equation (1) can be rewritten as follows:

$$E = (R - \Delta R)i - (R + \Delta R)i = -2\Delta R i \qquad (3)$$

This value $-2\Delta Ri$ is provided as the output for the zero point drift. The thermal detector described above is known in the art and is disclosed in Japanese Utility Model Publication No. 28956/1974.

FIG. 6 is an explanatory diagram for a description of the detection sensitivity of the apparatus according to this invention. More specifically, FIG. 6(a) is for the state A, while FIG. 6(b) is for the state B.

Referring to FIG. 6(a), an analysis gas, for instance a measurement gas containing CO gas, is allowed to flow in the first cell 50, while a reference gas, for instance $N_2$ gas, is allowed to flow in the second cell 51. In this case, the light quantity of the light beam $I_2$ irradiating the detection cell $A_2$ is greater than that of the light beam $I_1$ irradiating the detection cell $A_1$. Accordingly, the amount of light quantity absorption in the detection cell $A_2$ is greater than that in the detection cell $A_1$, and therefore the temperature and pressure of the detection cell $A_2$ are increased. As a result, the sealed gas is caused to flow from the detection cell $A_2$ to the detection cell $A_1$ in the direction of the arrow B. The heat of the detection element $G_2$ is absorbed by the flow of this sealed gas, that is, the temperature of the element $G_2$ is decreased, as a result of which its electrical resistance is decreased. On the other hand, the detection element $G_1$ is heated by the flow of the sealed gas the temperature of which has been increased by absorbing the heat of the detection element $G_2$, as a result of which the electrical resistance of the detection element $G_1$ is increased. The resistance variation of these detection elements will be expressed by $\Delta R_1$. The direction of the flow of the sealed gas which is caused by the optical unbalance which is due to the fact that the light beam $I_1$ is greater than the light beam $I_2$ at the beginning, will be designated by the arrow A. (The gas flow in the direction of the arrow A is merely theoretically considered present, but is does not exist in pratice.) The flow direction A of the sealed gas is opposite to the flow direction B of the same, and in general the flow rate in the direction B is higher than that in the direction A.

Accordingly, referring to the part (B) of FIG. 5, the resistances $R_1$ and $R_2$ are expressed by the following Equations (4) and (5), respectively.

$$R_1 = (R - \Delta R) + \Delta R_1 \quad (4)$$

$$R_2 = (R + \Delta R) - \Delta R_1 \quad (5)$$

In this case, the output EA provided in the detection circuit can be represented by the following Equation (6):

$$EA = R_1 \cdot i - R_2 \cdot i = -2\Delta R \cdot i + 2\Delta R_1 \cdot i \quad (6)$$

Referring to FIG. 6(b), the analysis gas is allowed to flow in the second cell 51, while the reference gas is allowed to flow in the first cell 50. In this case, the light quantity of the light beam $I_1$ irradiating the detection cell $A_1$ is greater than that of the light beam $I_2$ irradiating the detection cell $A_2$, as a result of which the amount of light quantity absorption in the detection bath $A_1$ is greater than that in the detection cell $A_2$, that is, the temperature of the detection cell $A_1$ becomes higher than that of the detection cell $A_2$ and, accordingly, the pressure of the detection cell $A_1$ becomes higher than that of the detection cell $A_2$. Therefore, the sealed gas is caused to flow from the detection cell $A_1$ to the detection cell $A_2$ in the direction of the arrow B which is opposite to the direction in FIG. 6(a). As a result, the resistance of the detection element $G_1$ is decreased as much as $\Delta R_1$, while the resistance of the detection element $G_2$ is increased as much as $\Delta R_1$. If the direction of the flow of the sealed gas which is caused by the fact that the light beam $I_1 >$ the light beam $I_2$ at the beginning is designated by the arrow A similarly as in the case of FIG. 6(a), this flow direction A is the same as the direction (B) mentioned above. Therefore, in the part (B) of FIG. 5, the resistances $R_1$ and $R_2$ can be expressed by the following Equations (7) and (8), respectively:

$$R_1 = (R - \Delta R) - \Delta R_1 \quad (7)$$

$$R_2 = (R + \Delta R) + \Delta R_1 \quad (8)$$

In this case, the output EB provided in the detection circuit is expressed by the following Equation (9):

$$EB = R_1 \cdot i - R_2 \cdot i = -2\Delta R \cdot i - 2\Delta R_1 \cdot i \quad (9)$$

Therefore, the measurement signal $E_O$ can be represented by the following Equation (10):

$$E_0 = EA - EB = (-2\Delta R \cdot i + 2\Delta R_1 \cdot i) - (2\Delta R \cdot i - 2\Delta R_1 \cdot i) = 2(2\Delta R_1 \cdot i) = 2E \quad (10)$$

$E = 2\Delta R_1 \cdot i$ in Equation (10) is representative of the output $L_1$ or $L_2$ of the detector 15. Accordingly, the measurement signal $E_0$ becomes twice the output $L_1$ or $L_2$ depending on the gas flow path switching states and, therefore, the sensitivity is increased twice. In Equation (10), the output $(-2\Delta R \cdot i)$ due to the zero point drift (Equation (3)) is cancelled, that is, the output $(-2\Delta R \cdot i)$ is not included in Equation (10). This means that the zero point drift is eliminated by switching the gas flow paths.

As is apparent from the above description, according to this invention, increase of the detection sensitivity and elimination of the zero point drift due to optical unbalance which are essential especially for low density gas analysis can be achieved by merely switching the flow paths of the measurement gas and the reference gas. The advantages of this effect should be well appreciated. Furthermore, as the measurement gas and the reference gas are alternately allowed to flow in the first cell and the second cell, the contamination of these cells is uniform and, thus, the optical balance is substantially maintained at all times.

With respect to the reference gas, the analysis component is eliminated by means of the low temperature combustion furnace; however, besides combustion, various chemical reactions and absorption may be readily employed. In the embodiment, the converter for converting CO gas into $CO_2$ is employed; however, if a converter for converting $H_2S$ gas into $SO_2$ gas or a converter for converting $NH_3$ gas into NO gas is employed, then $H_2S$ or $NH_3$ gas may be subjected to analysis. In this case, it is used as a $SO_2$ analyzer in which the gas passing through the converter is the reference case and the other gas is the sample gas. If a hydrogen carbide absorbent or a $SO_2$ absorbent is utilized, the apparatus may be employed as a hydrogen carbide meter or a $SO_2$ meter. Furthermore, the same object can be achieved by supplying the reference gas from a standard gas cylinder separately provided. In addition, the output holding function and the differential operation function may be achieved by using a digital computer or the like.

What is claimed is:

1. An infrared ray gas analyzing apparatus of the type having a first cell irradiated by a first light beam of infrared rays, a second cell irradiated by a second light beam of infrared rays, a gas supply means for supplying a sample gas to said first cell during a first period of time and a reference gas to said first cell during a second period of time, a detector for receiving and comparing said first and second light beams passed through said first and second cells and providing an output signal, and a signal process circuit having a first output signal holding circuit for storing the output of said detector during said first period of time, a second output signal holding circuit for storing the output of said detector during said second period of time and a differential amplifier to which the outputs of said first and second signal holding circuits are applied, said amplifier providing the analyzer output signal, wherein the improvement comprises:

said gas supply means supplying said reference gas to said second cell during said first period of time and supplying said sample gas to said second cell during said second period of time.

2. An infrared gas analyzing apparatus according to claim 1, wherein said gas supply means comprises:

first and second gas inlet passages for providing gas to said first and second chambers, respectively;

first and second three-way valves each having one input and two outputs, each of said three-way valves having one output connected to each said inlet passage;

a reference gas source for supplying reference gas to the inlet of said first three-way valve;

a sample gas source for supplying sample gas to the inlet of said second three-way valve; and valve control means for controlling said first and second three-way valves to thereby supply said reference and sample gases to opposite inlet passages during said first and second periods of time.

* * * * *